United States Patent [19]

Lin et al.

[11] Patent Number: 5,098,876
[45] Date of Patent: Mar. 24, 1992

[54] OLEFIN DISPROPORTIONATION CATALYST AND PROCESS

[75] Inventors: Jiang-Jen Lin; Randall T. DePue, both of Houston; Howard L. Fong, Sugar Land, all of Tex.

[73] Assignee: Shell Oil Company, Houston, Tex.

[21] Appl. No.: 572,736

[22] Filed: Aug. 27, 1990

[51] Int. Cl.$^5$ .............................................. B01J 31/00
[52] U.S. Cl. .................................... 502/150; 585/500
[58] Field of Search ............... 502/150; 585/500, 643, 585/645, 646, 647

[56] References Cited

U.S. PATENT DOCUMENTS

| | | | |
|---|---|---|---|
| 3,439,057 | 4/1969 | Calderon | 260/666 |
| 3,558,518 | 1/1971 | Zuech | 252/429 |
| 3,636,126 | 1/1972 | Menapace et al. | 260/683 D |
| 3,647,906 | 3/1972 | Farley | 260/683 D |
| 3,647,908 | 3/1972 | Medema et al. | 260/683 D |
| 3,652,704 | 3/1972 | Eades et al. | 260/683 D |
| 3,671,462 | 6/1972 | O'Hare et al. | 252/429 A |
| 3,686,136 | 8/1972 | Doyle | 252/429 B |
| 3,723,563 | 3/1973 | Bradshaw | 260/683 D |
| 3,829,523 | 8/1974 | Singleton | 260/683 D |
| 3,832,417 | 8/1974 | Ruhle | 260/683 D |
| 3,940,346 | 2/1976 | Zuech | 252/430 |
| 4,266,085 | 5/1981 | Kim et al. | 585/645 |

FOREIGN PATENT DOCUMENTS

| | | |
|---|---|---|
| 0268525 | 5/1988 | European Pat. Off. . |
| 61125438 | 11/1984 | Japan . |
| 62083043 | 10/1985 | Japan . |
| 6814835 | 10/1967 | Netherlands . |
| 1264973 | 6/1982 | U.S.S.R. . |
| 1251854 | 11/1971 | United Kingdom . |
| 1252799 | 11/1971 | United Kingdom . |
| 1284931 | 8/1972 | United Kingdom . |

*Primary Examiner*—Patrick P. Garvin
*Assistant Examiner*—E. D. Irzinski
*Attorney, Agent, or Firm*—Pamela J. McCollough

[57] ABSTRACT

This present invention relates to a disproportionation catalyst and to a process for preparing a disproportionation catalyst comprising forming a calcined composite comprising at least one of molybdenum and rhenium supported on an inorganic oxide support and contacting the calcined composite with an organoborane compound. The invention further relates to a process for the disproportionation of olefinic hydrocarbons comprising contacting at least one olefinic hydrocarbon with a catalyst comprising at least one of molybdenum and rhenium supported on an inorganic oxide support promoted with an organoborane compound. More specifically, the invention relates to the uses of an organoborane compound promoted molybdenum and rhenium supported on an inorganic oxide support for the production of linear alpha olefins from a mixture of internal olefins and ethylene. The invention also relates to the application of the described promoted catalyst for the production of 1,6-heptadiene and 1,6-octadiene from the reaction of cyclopentene with ethylene and propylene, respectively, and the fact that the presence of organoborane in the catalyst allows the reaction to be carried out at very mild temperature while obtaining high product selectivity.

29 Claims, No Drawings

5,098,876

OLEFIN DISPROPORTIONATION CATALYST AND PROCESS

FIELD OF THE INVENTION

This invention relates to a catalyst for use in the disproportionation of olefinic hydrocarbons comprising at least one of molybdenum and rhenium supported on an inorganic oxide support promoted with an organoborane compound and a process for the disproportionation of olefinic hydrocarbons comprising contacting at least one olefinic hydrocarbon with a catalyst comprising at least one of molybdenum and rhenium supported on an inorganic oxide support promoted with an organoborane compound.

This invention also relates to the application of such a catalyst system for the production of alpha olefins from internal olefins and ethylene. The same catalyst system is further used to prepare 1,6-heptadiene from cyclopentene and ethylene, and 1,6-octadiene from cyclopentene and propylene.

BACKGROUND OF THE INVENTION

Reactions of olefinic molecules in the presence of metal-containing catalysts to produce other olefinic molecules are known in the art as "disproportionation" reactions. The olefin disproportionation reaction can be visualized as the breaking of two existing double bonds between the first and second carbon atoms, and between the third and fourth carbon atoms, respectively, and the formation of two new double bonds, such as between the first and third carbon atoms and the second and fourth carbon atoms, respectively. A typical olefin disproportionation process is illustrated by U.S. Pat. No. 3,261,879, issued July 19, 1966, to Banks, wherein two similar non-symmetrical molecules of an olefin react in the presence of certain catalysts to produce one olefin of a higher carbon number and one olefin of a lower carbon number. For example, propylene disproportionates by the process of U.S. Pat. No. 3,261,879 to produce ethylene and butylenes.

A variation of this disproportionation process, which might be termed "reverse disproportionation" is illustrated by the Netherlands Patent No. 6514985 of British Petroleum Company Limited, published May 20, 1966, wherein, in one modification molecules of two dissimilar olefins are reacted to form two molecules of a single olefin product, e.g., ethylene and 2-butene react to form propylene.

Another variation of this process, being conveniently termed "ring opening disproportionation" to distinguish it from other variations, is disclosed by Netherlands Patent Application No. 6702703 of Phillips Petroleum Company, published Aug. 24, 1967, wherein a cyclic olefin and an acyclic olefin react to form a single product molecule. For example, ethylene reacts with cyclopentene by "ring opening disproportionation" to produce 1,6-heptadiene.

As used in this application, "disproportionation process" is meant to include all variations of disproportionations.

A variety of catalysts have been employed for conducting disproportionation reactions, such as those disclosed in U.S. Pat. No. 3,340,322, issued Sept. 5, 1967; U.S. Pat. No. 3,637,892, issued Jan. 25, 1972; U.S. Pat. No. 3,760,026, issued Sept. 18, 1973; U.S. Pat. No. 3,792,108, issued Feb. 12, 1974; U.S. Pat. No. 3,872,180, issued Mar. 18, 1975; and British Patent Specification No. 1,128,091, published Mar. 16, 1966. Among the catalysts that have been developed for disproportionation include inorganic refractory materials containing molybdenum and/or tungsten oxide.

Several patents disclose the use of promoter to enhance the disproportionation catalyst activity. Elemental metal promoters selected from the group consisting of barium, magnesium, tungsten, silicon, antimony, zinc, manganese and tin are disclosed in U.S. Pat. No. 4,568,788, issued Feb. 4, 1986, U.S. Pat. No. 4,522,936, issued June 11, 1985, U.S. Pat. No. 4,524,235, issued June 18, 1985 and U.S. Pat. No. 4,629,719, issued Dec. 16, 1986. In addition, organometallic compounds, such as aluminum and tin alkyls to promote solid catalysts including molybdenum and rhenium oxide for the disproportionation are disclosed in U.S. Pat. No. 4,454,368, issued June 12, 1984 and U.S. Pat. No. 3,829,523, issued Aug. 13, 1974.

It is an object of this invention to provide a catalyst system with novel promoters for olefin disproportionation at high activity. Another object is to provide a catalyst system adapted for high efficiency reaction and high selectivity to alpha olefin production from internal olefins and ethylene. The catalyst system is required to produce alpha olefins without significant olefin isomerization and ethylene polymerizations. It is a further object of this invention to maintain the improved results of the novel promoters of this catalyst system when used with a cyclic olefin reactant which is more reactive than a non-cyclic olefin and thus has a tendency to polymerize and an ethylene or propylene reactant to produce 1,6-heptadiene and 1,6-octadiene, which are useful chemical intermediates. Simply stated, the catalyst system may be used in the presence of a novel promoter and give desired cross-metathesis products from ethylene without side reactions.

An additional advantage is evidenced by the fact that reactions can be carried out at ambient temperature during the process, and the process requires no additional heat or energy activation sources.

The alpha olefin production from internal olefins and ethylene (i.e., ethenolysis) was reported by using $Re_2O_7$-on-alumina catalyst at 140° C. in U.S. Pat. No. 3,647,906, issued Mar. 7, 1972. However, the purities or selectivities to alpha olefins were not reported. In U.S. Pat. No. 3,658,927, issued Apr. 25, 1972 and *Journal of Catalysis*, 7, 269–276 (1967), a heterogeneous molybdenum oxide catalyst at high temperature was used for ethenolysis. The reaction produced alpha olefin with either low conversion or low selectivity.

Dienes prepared from cyclic olefins and ethylene using rhenium, molybdenum and tungsten catalysts are disclosed in U.S. Pat. No. 3,878,262, issued Apr. 15, 1975, U.S. Pat. No. 3,424,811, issued Jan. 28, 1969, and U.S. Pat. No. 3,792,102, issued Feb. 12, 1974. However, the use of molybdenum oxide catalysts to prepare dienes at high yield at room temperature is not disclosed. For example, in U.S. Pat. No. 3,981,940, issued Sept. 21, 1976, the synthesis of 1,9-decadiene from cyclooctene and ethylene using molybdenum oxide catalyst promoted by organoaluminum compound gave only 8% conversion at room temperature.

The present invention is therefore directed to a method of improving the activity of a disproportionation catalyst for converting olefins into olefins having different numbers of carbon atoms than the feed olefinic hydrocarbons, particularly to a method of improving the yield of alpha olefins and dienes prepared from ethylene reactions.

SUMMARY OF THE INVENTION

This present invention relates to a disproportionation catalyst comprising at least one of molybdenum and rhenium supported on an inorganic oxide support promoted with an organoborane compound and to a process for preparing a disproportionation catalyst comprising forming a calcined composite comprising at least one of molybdenum and rhenium supported on an inorganic oxide support and contacting the calcined composite with an organoborane compound. The invention further relates to a process for the disproportionation of olefinic hydrocarbons comprising contacting at least one olefinic hydrocarbon with a catalyst comprising at least one of molybdenum and rhenium supported on an inorganic oxide support promoted with an organoborane compound.

It has been found that the activity of a disproportionation catalyst can be improved by contacting the catalyst with an organoborane compound under conditions suitable for the organoborane compound to promote the activity of molybdenum and rhenium oxides. The activity of the disproportionation catalyst can be enhanced up to several orders of magnitude rate increase by the presence of organoborane, thus enabling the disproportionation reaction to be carried out at ambient temperature with advantages of high reaction productivity and product selectivity.

DESCRIPTION OF THE PREFERRED EMBODIMENTS

In the process of the instant invention, the disproportionation of an olefinic hydrocarbon is accomplished by contacting one or more olefinic hydrocarbons with a disproportionation catalyst comprising at least one of molybdenum and rhenium supported on an inorganic oxide support in the presence of an organoborane promoter.

Olefins which are suitable for disproportionation according to the instant invention are nontertiary, nonconjugated acyclic monoolefins and polyolefins having at least 2 carbon atoms per molecule including cycloalkyl, cycloalkenyl and aryl derivatives thereof; cyclic and polycyclic monoolefins and polyolefins having at least 3 carbon atoms per molecule including alkyl and aryl derivatives thereof; mixtures of the above olefins; and mixtures of ethylene and the above olefins. A useful group of olefin feed materials are acyclic olefins having carbon numbers ranging from $C_2$ to about $C_{50}$, preferably from $C_3$ to about $C_{30}$, and cyclic olefins having carbon numbers ranging from $C_4$ to about $C_{30}$. Nontertiary olefins are those olefins wherein each carbon atom, which is attached to another carbon number by means of a double bond, is also attached to at least one hydrogen atom.

Some specific examples of acyclic olefins suitable for disproportionation according to this invention are acyclic 1- and 2-alkenes, and alkyl and aryl derivatives thereof having from 2 to 30 carbon atoms per molecule. Some specific examples of such olefins are propylene, 1-butene, 2-butene, 1-pentene, 2-pentene, 1-hexene, 2-heptene, 1-octene, 2-nonene, 1-dodecene, 2-tetradecene, 1-hexadecene, 2-methyl-1-butene, 2-methyl-2-butene, 3-methyl-1-butene, 1-phenylbutene-2, 3-heptene and the like, and mixtures thereof.

Some specific examples of cyclic olefins suitable for disproportionation according to this invention are cyclobutene, cyclopentene, cycloheptene, cyclooctene, 5-n-propylcyclooctene, cyclodecene, cyclododecene, 3,3,5,5-tetramethylcyclononene, 3,4,5,6,7-pentaethylcyclodecene, 1,5-cyclooctadiene, 1,5,9-cyclododecatriene, 1,4,7,10-cyclododecatetraene, 6-methyl-6-ethylcyclooctadiene-1,4 and the like, and mixtures thereof.

The olefin feed should be essentially free of impurities which adversely affect the reaction. A subsequent reactivation of the catalyst to remove the effect of such impurities can be made repeatedly by heat treatment with air, using an inert gas to control burn-off temperature.

The disproportionation catalyst in the instant invention is prepared by forming a calcined composite comprising at least one of molybdenum and rhenium supported on an inorganic oxide support and contacting the calcined composite with a promoting amount of an organoborane compound. The inorganic oxide support comprises a solid usually containing a major proportion of silica or alumina. Such materials are commonly known as refractory oxides and include synthetic products as well as acid-treated clays or the crystalline alumina silicates known in the art as molecular sieves. Synthetic refractory oxides include silica, alumina, silica-alumina, silica-magnesia, silica-titania, alumina-titania, alumina-magnesia, boria-alumina-silica, alumina-zirconia, thoria and silica-titania-zirconia. Preferred inorganic oxide supports are alumina refractory oxides, i.e., refractory oxides containing a substantial proportion of alumina, e.g., at least about 90 percent by weight of alumina. Any conventional catalytic grade of alumina including the beta or gamma forms can be used. Generally, the inorganic oxide support has a surface area of at least 10 $m^2/g$ and preferably, the surface area is from about 25 $m^2/g$ to 800 $m^2/g$.

The molybdenum and/or rhenium can be combined with the inorganic oxide support in any conventional method such as dry mixing, ion-exchange, coprecipitation, impregnation and the like. For example, a 10–100 mesh alumina can be impregnated with an aqueous solution containing molybdenum salts, such as ammonium heptamolybdate or ammonium dimolybdate.

In a preferred embodiment, the disproportionation catalyst in the instant invention is a molybdenum oxide prepared by impregnating alumina with an aqueous molybdenum impregnation solution. The aqueous molybdenum solution consists of a water-soluble source of molybdenum oxide such as ammonium heptamolybdate or ammonium dimolybdate dissolved in water. Hydrogen peroxide may also be used to aid in solution preparation in some cases. For example, the molybdenum solution can be prepared by adding hydrogen peroxide to the solution in an amount in the range of from about 0.1 to about 1.0 mole of hydrogen peroxide per mole of molybdenum. Optionally, a suitable soluble amine compound such as monoethanolamine, propanolamine or ethylenediamine may be added to the molybdenum solution in order to aid in stabilization of the solution.

Following impregnation, the resulting material is dried and calcined. Drying is accomplished by conventional means. It may be carried out by forced draft drying, vacuum drying air drying or similar means. Drying temperatures are not critical and depend upon the particular means utilized for drying. Drying temperatures will typically range from about 50° C. to about 150° C.

After drying, the material is calcined to produce the finished catalyst. The material may be calcined in an oxidizing or neutral atmosphere, although air is preferred. However, if binders and/or lubricants are used the material is heated in an oxygen-containing atmosphere, preferably air, in order to burn out the binders and lubricants. Calcining temperatures will typically range from about 300° C. to about 600° C. Burn-out temperatures will depend on the concentration of oxygen in the burn-out atmosphere as well as the burn-out time involved. Typically, burn-out temperatures will range from about 300° C. to about 600° C. Drying, calcining and burn-out may be combined in one or two steps. Most frequently the calcining and/or burn-out steps are combined using an oxygen-containing atmosphere.

The final calcined composites typically contain from about 1 percent by weight to about 18 percent by weight, preferably from about 5 percent by weight to about 15 percent by weight, and more preferably from about 6 percent by weight to about 12 percent by weight molybdenum and from about 1 percent by weight to about 20 percent by weight, preferably from about 5 percent by weight to about 15 percent by weight, and more preferably from about 6 percent to about 12 percent by weight rhenium. When mixtures of molybdenum and rhenium are utilized, the final catalyst typically contains from about 1 percent by weight to about 32 percent by weight molybdenum and/or rhenium. These types of catalysts are well known in the art and reference can be prepared according to the prior art, such as but not limited to aforementioned U.S. Pat. No. 3,261,879 and U.S. Pat. No. 3,365,513 (both of which are incorporated by reference herein) for more specific details about these types of catalysts.

The supported molybdenum and/or rhenium oxide composites are preferably subjected to a pretreatment prior to contact with the organoborane compound. While pretreatment is usually accomplished by contacting the catalyst with an oxygen-containing gas at elevated temperatures, other activation methods such as heating under a vacuum, or contact with various gases such as nitrogen or argon at high temperatures, can be used. One function served by this type of pretreatment is to convert the molybdenum and/or rhenium components into the form of the oxide if these components are not initially provided in these forms. The temperature, contact times, and other conditions of pretreatment have been reported in the prior art and are generally the same conditions which are utilized to activate a disproportionation catalyst. Typically, the pretreatment conditions include a temperature in the range of from about 300° C. to about 900° C. for about 30 minutes to about 24 hours.

In order to obtain the active catalyst composition of the instant invention, the molybdenum and/or rhenium oxide supported composition is treated with an organoborane compound. The promoting organoborane compound can be combined with the molybdenum or rhenium oxide supported compositions in any suitable manner. For example, the molybdenum and/or rhenium oxide supported composition can be impregnated with a liquid diluent containing the organoborane compound at ambient temperature up to 150° C. After impregnation, the catalyst is then heated in an inert atmosphere, such as nitrogen or argon, to remove the liquid diluent. The temperature employed in removing the diluent and activating can vary widely; however, temperatures in the range of about 25° C. to about 200° C. are preferred. If desired, the promoter can be applied to the supported molybdenum and/or rhenium oxide in a reaction zone by spraying or otherwise contacting with the oxide. It is also contemplated that the promoter can be introduced along with the olefin feed as a means for contacting with supported molybdenum and/or rhenium oxide.

In accordance with the invention, the calcined molybdenum and/or rhenium oxide refractory materials are treated with an effective promoting amount of an organoborane compound and heated under conditions to form a promoted catalyst. The organoborane promoter should have at least one boron to carbon bond. The preferred organoborane compounds are alkylboranes such as triethylborane, tri-sec-butylborane, tri-n-butylborane, trimethylborane, tricyclohexylborane and the like, with tri-sec-butylborane and triethylborane being preferred. Suitable molybdenum or rhenium oxide/organoborane molar ratios are typically in the range of from about 0.1 to about 50, preferably from about 1 to about 30 and more preferably, from about 1.5 to about 25.

The disproportionation process of the invention can be carried out either batchwise or continuously, using a fixed catalyst bed, or a stirrer equipped reactor or other mobile catalyst contacting process as well as any other well known contacting technique. Preferred reaction conditions, e.g., temperature, pressure, flow rates, etc., vary somewhat depending upon the specific catalyst composition, the particular feed olefin, desired products, etc. The process is carried out at temperatures ranging from about −10° C. to about 350° C. and at pressures in the range of about 50 psig to about 2000 psig. The disproportionation reaction is usually effected in a liquid phase and if desired, liquid reaction diluents are utilized. Examples of suitable diluents are hydrocarbons free from aliphatic unsaturation, such as cyclic or alicyclic alkanes of from 6 to 12 carbon atoms, i.e. hexane, isooctane and cyclohexane. Also exemplary would be monoaromatic compounds such as benzene and toluene. If the diluent is added, it is present in amounts up to 20 moles of diluent per mole of olefinic reactants.

The operable range of contact time for the process of this invention depends primarily upon the operating temperature and the activity of the catalyst, which is influenced by surface area, promoter concentration, activation temperature, etc. In general, the distribution of products is not drastically altered by variation in contact time. Shorter contact times are usually associated with higher temperatures. With proper selection of conditions and contact times, very high efficiency of conversion to desired products can be obtained.

With a fixed bed reactor, continuous flow operation at pressures in the range of about 50 psig to about 2000 psig, preferably about 100 psig to about 1000 psig, with catalysts having densities ranging from about 0.3 gram per cc to about 2.0 gram per cc and surface areas greater than about 100 $m^2/g$, and at temperatures in the range of about −10° C. to about 350° C., preferably at room temperature, weight hourly space velocities in the range of about 0.1 to about 10.0 parts by weight of olefinic hydrocarbon feed per part by weight of catalyst per hour are suitable. The space velocity is adjusted according to changes in density of feed due to change of pressure or temperature, and variation in reaction temperature and the activity of the catalyst.

In one embodiment, desired carbon numbers of internal olefins can be prepared by disproportionation of less desirable alpha or internal olefins. By using organoborane promoted heterogeneous catalysts, for example, 1-decene can be converted into 9-octadecene and ethylene (reaction 1):

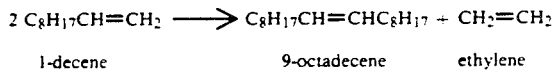

and a mixture of internal decene isomers can be converted to a number of internal olefins ranging from $C_3$ to $C_{18}$. Some of these products are useful as detergent intermediates. When the promoted catalyst in the instant invention is utilized in these reations, the advantages over the use of a non-promoted catalyst are numerous; the reactions can be carried out at room temperature, increased reaction rate can be achieved, and the reaction can be run conveniently without additional energy supply.

In another embodiment, $C_3$ to $C_9$ alpha olefins with good purity can be produced at room temperature from the disproportionation of a mixture of internal decenes and ethylene as described in reaction 2:

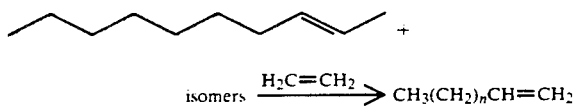

wherein n=0 to 6. Alpha olefins are used to produce a number of useful products, including comonomers for high density polyethylene (HDPE), linear low density polyethylene (LLDPE), intermediates for synthetic lube oils and lube oil additives, surfactants, paper sizings and specialty chemicals.

In another embodiment, dienes and trienes can be produced by disproportionating cyclic olefins with ethylene. By way of illustration, cyclopentene can be reacted with ethylene to form 1,6-heptadiene, cyclooctene with ethylene to form 1,9-decadiene and 1,5-cyclooctadiene with ethylene to form 1,5-hexadiene. The disproportionation reaction is conducted by contacting cyclopentene with an excess of ethylene in the presence of the catalyst of the instant invention, a disproportionation catalyst comprising at least one of molybdenum and rhenium supported on an inorganic oxide support and an organoborane promoter. When the promoted catalyst in the instant invention is utilized in this reaction, the advantages over the use of a non-promoted catalyst are numerous; the reaction can be carried out at room temperature, and increased reaction rates can be achieved, conversions of at least about 80% can be achieved; and undesired side reactions, such as double bond isomerization, are minimal.

In another embodiment, cyclopentene can be reacted with propylene to produce 1,6-octadiene as the major product. While trienes and tetrenes are formed as by-products in this disproportionation reaction, the by-products can be recycled to produce the desired dienes, thus making the reaction quite efficient. As is true with the previously described embodiment, when the promoted catalyst in the instant invention is utilized in this disproportionation reaction, the advantages over the use of a non-promoted catalyst are numerous; the reaction can be carried out at room temperature, increased reaction rates can be achieved; increased conversions can be achieved; and undesired side reactions, such as double bond isomerization, are minimal.

The ranges and limitations provided in the instant specification and claims are those which are believed to particularly point out and distinctly claim the instant invention. It is, however, understood that other ranges and limitations that perform substantially the same function in substantially the same manner to obtain the same result are intended to be within the scope of the instant invention as defined by the instant specification and claims.

The process of the instant invention will be further described below by the following examples which are illustrative and which are not to be construed as limiting the invention.

ILLUSTRATIVE EMBODIMENTS

Catalyst Preparation

The disproportionation catalysts utilized in the examples below were prepared using a conventional dry pore volume impregnation technique.

A 12% $MoO_3/Al_2O_3$ catalyst was prepared as follows. A solution suitable for impregnating 88 grams of calcined alumina support with a pore volume of 1.0 cm/g was prepared as follows. An impregnation solution was made by combining 14.7 grams of ammonium heptamolybdate, 5.7 grams of 30% hydrogen peroxide and 32.4 grams of deionized water or enough water to bring the solution to a total volume of 88 milliliters. After adding the entire solution to the alumina support in several small portions with intermediate agitations, the impregnated support was dried overnight at 150° C. and calcined in air for at least 2 hours at 550° C. and in nitrogen for at least 1 hour at 550° C.

A 6% $MoO_3/Al_2O_3$ catalyst was prepared as follows. A solution suitable for impregnating 88 grams of calcined alumina support with a pore volume of 1.0 cm/g was prepared as follows. An impregnation solution was made by combining 7.4 grams of ammonium heptamolybdate, 2.9 grams of 30% hydrogen peroxide and 16.2 grams of deionized water or enough water to bring the solution to a total volume of 44 milliliters. After adding the entire solution to the alumina support in several small portions with intermediate agitations, the impregnated support was dried overnight at 150° C. and calcined in air for at least 2 hours at 550° C. and in nitrogen for at least 1 hour at 550° C.

DISPROPORTIONATION OF 1-DECENE

Example 1

To a 50 ml oven-dried round bottomed flask equipped with a magnetic stir bar and a three-way stopcock was added 12% molybdenum oxide on alumina catalyst (2.0 g, 1.7 mmoles $MoO_3$), 1-decene (20 ml, 105 mmoles) and tri-sec-butylborane (0.031 g, 0.17 mmoles) under nitrogen atmosphere. The mixture was then stirred at room temperature. Periodically, samples were taken and analyzed by glc. The products were further identified by gc-mass spectrometry and other analytic means. This example demonstrates high catalyst activity at room temperature for 1-decene disproportionation to $C_{18}$ olefins. The results of the disproportionation reaction are presented in Table I.

Example 2

The disproportionation was carried out in the same manner as Example 1 except that triethylborane (0.017 g, 0.17 mmoles) was used in place of tri-sec-butylborane as promoter. The results of the disproportionation reaction are presented in Table I.

Example 3

The disproportionation was carried out in the same manner as Example 1 except that 9-BBN (9-borabicyclo[3,3,1]nonane) (0.042 g, 0.35 mmoles) was used in place of tri-sec-butylborane as promoter. The results of the disproportionation reaction are presented in Table I.

Comparative Example A

The disproportionation was carried out in the same manner as Example 1 except that no promoter was present. The results of the disproportionation reaction are presented in Table I.

As can be seen in Table I, low yield to $C_{18}$ olefins was obtained.

Example 4

To a 50 ml oven-dried round bottomed flask equipped with a magnetic stir bar and a three-way stopcock was added 6% molybdenum oxide on alumina catalyst (2.0 g, 0.83 mmole $MoO_3$), 1-decene (20 ml, 105 mmoles) and tri-sec-butylborane (0.031 g, 0.17 mmole) under nitrogen atmosphere. The mixture was then stirred at room temperature. Periodically, samples were taken and analyzed by glc. The products were further identified by gc-mass spectrometry and other analytic means. This example demonstrates high catalyst activity at room temperature for 1-decene disproportionation to $C_{18}$ olefins. The results of the disproportionation reaction are presented in Table I.

Example 5

The disproportionation was carried out in the same manner as Example 4 except that triethylborane (0.017 g, 0.17 mmoles) was used in place of tri-sec-butylborane as promoter. The results of the disproportionation reaction are presented in Table I.

Example 6

The disproportionation was carried out in the same manner as Example 4 except that 9-BBN (9-borabicyclo[3,3,1]nonane) (0.042 g, 0.35 mmoles) was used in place of tri-sec-butylborane as promoter. The results of the disproportionation reaction are presented in Table I.

Comparative Example B

The disproportionation was carried out in the same manner as Example 4 except that no promoter was present. The results of the disproportionation reaction are presented in Table I.

As can be seen in Table I, low yield to $C_{18}$ olefins was obtained.

TABLE I

DISPROPORTIONATION OF 1-DECENE

| | Catalyst | Borane Added (Mmoles) | Reaction Time (hr) | Unreacted Decenes | $C_{15}=$ | $C_{16}=$ | $C_{17}=$ | $C_{18}=$ |
|---|---|---|---|---|---|---|---|---|
| Example 1 | 12% $MoO_3/Al_2O_3$ | Sec-Bu$_3$B (0.17) | 1 | 31 | 1 | 3 | 9 | 36 |
| | | | 3 | 18 | 2 | 5 | 14 | 35 |
| | | | 18 | 9 | 5 | 10 | 18 | 21 |
| Example 2 | 12% $MoO_3/Al_2O_3$ | Et$_3$B (0.17) | 1 | 37 | 0 | 2 | 4 | 46 |
| | | | 3 | 26 | 1 | 3 | 8 | 48 |
| | | | 18 | 13 | 2 | 5 | 15 | 47 |
| Example 3 | 12% $MoO_3/Al_2O_3$ | 9-BBN (0.35) | 1 | 73 | 0.4 | 0.7 | 0.8 | 16 |
| | | | 3 | 39 | 0.3 | 2 | 3 | 45 |
| | | | 18 | 23 | 0.8 | 3 | 9 | 50 |
| Comparative Example A | 12% $MoO_3/Al_2O_3$ | None | 3 | 84 | ~0 | ~0 | ~0 | 7 |
| Example 4 | 6% $MoO_3/Al_2O_3$ | Sec-Bu$_3$B (0.17) | 1 | 28 | 0 | 2 | 2 | 61 |
| | | | 3 | 26 | 1 | 2 | 2 | 62 |
| | | | 18 | 17 | 1 | 3 | 8 | 59 |
| Example 5 | 6% $MoO_3/Al_2O_3$ | Et$_3$B (0.17) | 1 | 42 | ~0 | 2 | 2 | 46 |
| | | | 3 | 16 | 0.5 | 2 | 4 | 61 |
| | | | 18 | 16 | 1 | 4 | 11 | 54 |
| Example 6 | 6% $MoO_3/Al_2O_3$ | 9-BBN (0.35) | 3 | 56 | 0 | 1 | 1 | 33 |
| | | | 18 | 19 | 1 | 3 | 9 | 56 |
| Comparative Example B | 6% $MoO_3/Al_2O_3$ | None | 3 | 93 | 0 | 0 | 0 | 1 |

DISPROPORTIONATION OF INTERNAL DECENES AND ETHYLENE

Example 7

Example 7 involving the disproportionation of internal olefins and ethylene (ethenolysis) was carried out in a 80 mL autoclave which was charged with 4.0 grams of catalyst and a magnetic stir bar. The catalyst was activated with a solution of the required amount of tri-sec-butylborane (0.078 g, 0.43 mmoles) to give a molybdenum oxide to tri-sec-butylborane molar ratio (mole Mo/B) of 7.9. The catalyst was then suspended in 20.0 ml of internal decene. The borane solution was added to the catalyst either before or after pressurization with ethylene. The reaction was performed at ambient temperature (approximately 20.8°–24.8° C.) under continuous pressure of purified ethylene, which was supplied on demand. During sample collection, significant amounts of volatiles were lost. By use of an internal standard, conversions are estimated to be at least 10% greater than indicated by the amount of unreacted i-decene that remains. The results are presented in Table II.

Examples 8–9

Examples 8–9 were carried out in the same manner as Example 7, except that different molybdenum oxide to tri-sec-butylborane molar ratios were use. The results are presented in Table II.

Comparative Example C

Comparative Example C was carried out in the same manner as Examples 7, except that no promoter was present. The results of the disproportionation reaction are presented in Table II.

It is noted a mixture of $C_5$ to $C_9$ alpha olefins were produced at ambient temperatures when the organoborane promoter was present. Reaction rates ranging from 3.9–4.9 g i-decene conversion/g catalyst/hr can be achieved. The importance of the organoborane promoter in the catalyst was evidenced in Comparative Example C, which showed no significant amount of alpha olefins was produced when the promoter was absent from the system. It is noted that the high internal olefin conversion at 86–96% can be achieved within 4.0 hr reaction time and, in some cases, alpha olefins product selectivity were >99% for 1-pentene, >99% for 1-hexene, >98.4% for 1-heptene, >97.5% for 1-octene and >96.9% for 1-nonene.

taken. The products were analyzed by gc, gc/mass spectrum and nmr. The results are summarized in Table III.

The analyses showed in some cases >90% conversion of cyclopentene with product selectivities for 1,6-octadiene (40% selectivity), 1,6-heptadiene (13%), 2,7-nonadiene (8%), trienes ($C_{12}$, $C_{13}$ and $C_{14}$, 26%) and tetraenes ($C_{17}$, $C_{18}$ and $C_{19}$, 10%). The cis- and trans-1,6-octadiene products were isolated by distillation and identified by nmr and gc-mass spectrometry. Product linearities, determined by in situ hydrogenation/gc, were 98.7% for $C_7$, 99.5% for $C_8$, 98.3% for $C_9$, 98.6% for $C_{12}$, 99.3% for $C_{13}$, 98.9% for $C_{14}$, 97.0% for $C_{17}$ and 97.0% for $C_{18}$. The high linearity indicates the good selectivity for metathesis products. The recycle of heavy products, $C_{12}$–$C_{14}$ trienes and $C_{17}$–$C_{19}$ tetraenes, with propylene to produce more $C_7$–$C_9$ dienes has also been demonstrated.

Examples 11–15

TABLE II

| | Catalyst | | Conditions | | Product Distribution | | | | | | |
|---|---|---|---|---|---|---|---|---|---|---|---|
| | Wt % MoO₃ | Mole Mo/B | $C_2=$ PSI | Reaction Time (Hrs) | Weight Percent (Uncorrected) | | | | | | |
| | | | | | $C_5$ | $C_6$ | $C_7$ | $C_8$ | $C_9$ | $C_{10}$ | $C_{11}^-$ |
| Example 7 | 12.0 | 7.9 | 1300 | 0.5 | 0.6 | 2.3 | 7.2 | 11.9 | 19.5 | 54.6 | 2.1 |
| | | | 1300 | 1.0 | 1.0 | 3.7 | 11.9 | 19.9 | 32.4 | 25.3 | 3.6 |
| | | | 1300 | 2.0 | 4.1 | 10.9 | 20.0 | 21.8 | 28.2 | 9.1 | 3.3 |
| | | | 1300 | 4.0 | 2.9 | 9.7 | 20.3 | 24.1 | 32.1 | 4.0 | 4.0 |
| Example 8 | 12.0 | 5.7 | 1300 | 0.5 | 1.2 | 5.3 | 11.9 | 13.5 | 18.7 | 45.3 | 2.7 |
| | | | 1300 | 1.0 | 1.0 | 4.5 | 13.5 | 18.0 | 26.5 | 31.2 | 3.5 |
| | | | 1300 | 2.0 | 1.0 | 4.6 | 15.3 | 23.0 | 34.6 | 15.0 | 4.2 |
| | | | 1300 | 4.0 | 1.3 | 6.0 | 17.8 | 24.7 | 35.8 | 7.0 | 4.7 |
| Example 9 | 12.0 | 1.9 | 1300 | 0.5 | 0.5 | 2.1 | 6.5 | 9.7 | 15.4 | 61.9 | 2.1 |
| | | | 1300 | 1.0 | 0.8 | 3.4 | 9.7 | 13.2 | 19.8 | 48.9 | 2.4 |
| | | | 1300 | 2.0 | 0.9 | 3.9 | 11.5 | 16.5 | 25.1 | 36.6 | 3.3 |
| | | | 1300 | 4.0 | 1.1 | 5.1 | 14.2 | 19.0 | 28.3 | 23.6 | 3.4 |
| Comparative Example C | 12.0 | No Promoter | 1300 | 4.0 | 0.01 | 0.03 | 0.1 | 0.2 | 0.2 | 97.5 | 0.2 |

DISPROPORTIONATION OF CYCLOPENTENE AND PROPYLENE

Example 10

12% $MoO_3$-on-alumina catalyst (4.0 g), cyclopentene (14.7 g, 210 mmoles), propylene (16.8 g, 400 mmoles) and tri-sec-butylborane (0.03 g, 0.17 mmoles) were changed into a stainless steel autoclave equipped with a stirrer, a pressure gague, and a pressure relief valve. The mixtures were stirred at room temperature for 2 hours. An analytical sample at 1 hour reaction time was Examples 11–15 are carried out in the same manner as Example 10 except that different molar ratios of molybdenum oxide to tri-sec-butylborane were used. The results are summarized in Table III.

Comparative Example D

Comparative Example D was carried out in a manner similar to that in Example 10 except that there was no tri-sec-butylborane promoter added. The results are summarized in Table III.

TABLE III

DISPROPORTIONATION OF CYCLOPENTENE AND PROPYLENE

| Example | Starting Materials | | Catalyst % MoO₃ | Promoter Mo/B[b] | Conditions | Conv. % (Cyclopentene) | Product Distribution %[a] | | | | | | | | |
|---|---|---|---|---|---|---|---|---|---|---|---|---|---|---|---|
| | Cyclopentene (mm) | Propylene (mm) | | | | | Dienes | | | Trienes | | | Tetraenes | | |
| | | | | | | | $C_7H_{12}$ | $C_8H_{14}$ | $C_9H_{16}$ | $C_{12}H_{20}$ | $C_{13}H_{22}$ | $C_{14}H_{24}$ | $C_{17}H_{28}$ | $C_{18}H_{30}$ | $C_{19}H_{32}$ |
| 10 | 210 | 400 | 12 | 20 | 25° C./ 2 hrs | 70 | 13 | 40 | 8 | 7 | 15 | 4 | 3 | 6 | 2 |
| 11 | 210 | 360 | 12 | 20 | 25–30° C./ 1 hr | >90 | 15 | 35 | 10 | 6 | 12 | 9 | 4 | 4 | 1 |
| 12 | 320 | 680 | 9 | 7.5 | 20–29° C./ 2 hr | >90 | 13 | 30 | 10 | 6 | 13 | 5 | 4 | 8 | 3 |
| 13 | 430 | 640 | 6 | 5 | 25° C./ 2 hrs | 89 | 4 | 15 | 8 | 6 | 20 | 9 | 7 | 21 | 8 |
| 14 | 320 | 300 | 12 | 7.5 | 24–30° | 83 | 6 | 26 | 5 | 5 | 19 | 3 | 4 | 13 | 2 |

TABLE III-continued

DISPROPORTIONATION OF CYCLOPENTENE AND PROPYLENE

| Example | Starting Materials Cyclopentene (mm) | Propylene (mm) | Catalyst % MoO$_3$ | Promoter Mo/B$^{(b)}$ | Conditions | Conv. % (Cyclopentene) | Product Distribution %$^{(a)}$ Dienes | | | Trienes | | | Tetraenes | | |
|---|---|---|---|---|---|---|---|---|---|---|---|---|---|---|---|
| | | | | | | | C$_7$H$_{12}$ | C$_8$H$_{14}$ | C$_9$H$_{16}$ | C$_{12}$H$_{20}$ | C$_{13}$H$_{22}$ | C$_{14}$H$_{24}$ | C$_{17}$H$_{28}$ | C$_{18}$H$_{30}$ | C$_{19}$H$_{32}$ |
| 15 | 320 | 660 | 12 | 5 | C./2 hrs 25° C./2 hrs | >90 | 13 | 26 | 10 | 7 | 13 | 6 | 6 | 13 | 5 |
| Comparative Example D | 320 | 700 | 12 | No Promoter | C./2 hr 24–30° | <5 | — | — | — | — | — | — | — | — | — |

$^{(a)}$GC area %; C$_3$, C$_4$ olefins and high molecular polyenes, are not included
$^{(b)}$Sec-Bu$_3$B was used, in molar ratio.

I claim as my invention:

1. A disproportionation catalyst comprising at least one of molybdenum and rhenium supported on an inorganic oxide support promoted with an organoborane compound.

2. The catalyst of claim 1 wherein said organoborane compound is selected from the group consisting of triethylborane, tri-sec-butyulborane, diethylborane, ethylborane, tricyclohexylborane, 9-borabicyclo[3,3,1]nonane, and mixtures thereof.

3. The catalyst of claim 2 wherein said organoborane is selected from triethylborane and tri-sec-butylborane.

4. The catalyst of claim 2 wherein the molybdenum and/or rhenium/organoborane molar ratio is in the range of from about 0.1 to about 50.

5. The catalyst of claim 4 wherein the molybdenum and/or rhenium/organoborane molar ratio is in the range of from about 1 to about 30.

6. The catalyst of claim 5 wherein the molybdenum and/or rhenium/organoborane molar ratio is in the range of from about 1.5 to about 25.

7. The catalyst of claim 1 wherein said disproportionation catalyst contains from about 1 percent by weight to about 18 percent by weight molybdenum.

8. The catalyst of claim 7 wherein said disproportionation catalyst contains from about 5 percent by weight to about 15 percent by weight molybdenum.

9. The catalyst of claim 8 wherein said disproportionation catalyst contains from about 6 percent by weight to about 12 percent by weight molybdenum.

10. The catalyst of claim 1 wherein said disproportionation catalyst contains from about 1 percent by weight to about 20 percent by weight rhenium.

11. The catalyst of claim 10 wherein said disproportionation catalyst contains from about 5 percent by weight to about 15 percent by weight rhenium.

12. The catalyst of claim 11 wherein said disproportionation catalyst contains from about 6 percent by weight to about 12 percent by weight rhenium.

13. The catalyst of claim 1 wherein said inorganic oxide support is selected from the group consisting of silica, alumina, silica-alumina, silica-magnesia, silica-titania, alumina-titania, alumina-magnesia, boria-alumina-silica, alumina-zirconia, thoria, silica-titania-zirconia and mixtures thereof.

14. The catalyst of claim 13 wherein said inorganic oxide support is alumina.

15. A process for preparing a disproportionation catalyst comprising forming a calcined composite comprising at least one of molybdenum and rhenium supported on an inorganic oxide support and contacting the calcined composite with an organoborane compound.

16. The process of claim 15 wherein said organoborane compound is selected from the group consisting of triethylborane, tri-sec-butylborane, tricyclohexylborane, diethylborane, ethylborane, 9-borabicyclo[3,3,1]nonane and mixtures thereof.

17. The process of claim 16 wherein said organoborane is selected from triethylborane and tri-sec-butylborane.

18. The process of claim 16 wherein the molybdenum and/or rhenium/organoborane molar ratio is in the range of from about 0.1 to about 50.

19. The process of claim 18 wherein the molybdenum and/or rhenium/organoborane molar ratio is in the range of from about 1 to about 30.

20. The process of claim 19 wherein the molybdenum and/or rhenium/organoborane molar ratio is in the range of from about 1.5 to about 25.

21. The process of claim 15 wherein said disproportionation catalyst contains from about 1 percent by weight to about 18 percent by weight molybdenum.

22. The process of claim 21 wherein said disproportionation catalyst contains from about 5 percent by weight to about 15 percent by weight molybdenum.

23. The process of claim 22 wherein said disproportionation catalyst contains from about 6 percent by weight to about 12 percent by weight molybdenum.

24. The process of claim 15 wherein said disproportionation catalyst contains from about 1 percent by weight to about 20 percent by weight rhenium.

25. The process of claim 24 wherein said disproportionation catalyst contains from about 5 percent by weight to about 15 percent by weight rhenium.

26. The process of claim 25 wherein said disproportionation catalyst contains from about 6 percent by weight to about 12 percent by weight rhenium.

27. The process of claim 15 wherein said inorganic oxide support is selected from the group consisting of silica, alumina, silica-alumina, silica-magnesia, silica-titania, alumina-titania, alumina-magnesia, boria-alumina-silica, alumina-zirconia, thoria, silica-titania-zirconia and mixtures thereof.

28. The process of claim 27 wherein said inorganic oxide support is alumina.

29. The process of claim 15 wherein said composite is calcined by activating with an oxygen-containing gas at a temperature of from about 300° C. to about 800° C. prior to the addition of the organoborane promoter.

* * * * *